US00PP11269P

United States Patent [19]

Kordes

[11] Patent Number: Plant 11,269

[45] Date of Patent: Mar. 7, 2000

[54] FLORIBUNDA ROSE PLANT NAMED 'KORMILLER'

[75] Inventor: Wilhelm Kordes, Sparrieshoop, Germany

[73] Assignee: Bear Creek Gardens, Inc., Medford, Oreg.

[21] Appl. No.: 08/985,371

[22] Filed: Dec. 4, 1997

[51] Int. Cl.[7] ..... A01H 5/00

[52] U.S. Cl. ..... Plt./148

[58] Field of Search ..... Plt./22, 26, 25, Plt./11, 18, 141, 146, 148, 130, 135, 137

*Primary Examiner*—Howard J. Locker

*Attorney, Agent, or Firm*—Klarquist Sparkman Campbell Leigh & Whinston, LLP

[57] ABSTRACT

Floribunda rose plant having high production of long vase life cut roses of pastel pink flower color on strong, straight stems with few thorns.

1 Drawing Sheet

The present invention relates to a new and distinct variety of rose plant of the floribunda class which was originated by me by crossing an unnamed seedling, with an unnamed seedling.

The primary objective of this breeding was to produce a new rose variety having the good production, good vase life, and good shipping qualities of the pink unnamed female parent combined with the very good production and good vase life of the unnamed pink male breedling line. The objective was substantially achieved, along with other desirable improvements, as evidenced by the following unique combination of characteristics that are outstanding in the new variety and that distinguish it from its parents, as well as from all other varieties of which I am aware:

1. Very good cut flower production;
2. Long vase life;
3. Few thorns;
4. Strong, straight stems;
5. Attractive, pastel pink flower color.

KORmiller is a vigorous, upright, well-branched floribunda bred for cut flower production. Yield is 180–200 per square meter of greenhouse (26–29 flowers per plant per year). Long vase life of 16–19 days and its few thorns make this an ideal cut rose.

Asexual reproduction of this new variety by budding, as performed at Sparrieshoop, Germany and Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—Rosa hybrida.

*Commercial.*—Floribunda.

FLOWER

Observations made from specimens grown in a greenhouse environment at Sparrieshoop, Germany and at Somis, Calif. from January, 1996–August 1997.

Blooming habit: Continuous.

Bud:

*Size.*—One and one-half inches long when the petals start to unfurl.

*Form.*—The bud form is long, pointed ovoid but somewhat blunt at the tip.

*Color.*—When sepals first divide, bud color is Orange Group 29C. When half blown, the upper sides of the petals are Orange-Red Group 32D on the outer two-thirds of a petal, the inner third of a petal progressively changes color down the petal from Yellow Group 3D to Yellow Group 3C; and the outer two-thirds of the lower sides of the petals are Orange Group 29C, the inner one-third progressively changing down the petal to Yellow Group 3D.

*Sepals.*—Color: Green Group 138B. Surface texture: Covered in fine hairs. There are three normally to heavily appendaged sepals. There are two unappendaged sepals with hairy edges.

*Receptacle.*—Color: Green-Yellow Group 146C. Shape: Funnel. Size: Medium (5/16" long ×1/4" wide). Surface: Smooth.

*Peduncle.*—Length: Short (2-1/2"). Surface: Smooth. Color: Medium green (Green Group 137C). Strength: Stiff, erect.

Bloom:

*Size.*—Medium. Average open size is three and one-half to four inches.

*Borne.*—Singly.

*Stems.*—Medium (18–22"), strong.

*Form.*—When first open: High centered. Permanence: Retains its form to the end; outer petals curl back some quilling.

*Petalage.*—Number of petals under normal conditions: 25–30.

*Color.*—The outer two-thirds of the upper sides of the petals are Orange-Red Group 32D, then progressively changing down the petal to Yellow Group 3D and then to Yellow Group 3C. The outer two-thirds of the reverse sides of the petals are Orange Group 29C, progressively changing down the petal to Yellow Group 3D. The base of each petal has a small (3/16"×3/16"), bright yellow, (Yellow Group 3B), half moon at the point of attachment. The major color on the upper side is Orange-Red Group 32D.

*Variegations.*—Occasional greenish-white streak on the guard petals.

*Discoloration*.—At the end of the first day: No change. At the end of the third day: No change. Color holds until day seven or eight on the plant then fades to Orange Group 29D before petals drop by day ten. In the vase, the color remains constant through day sixteen to eighteen when petals drop.

*Fragrance*.—Slight.

Petals:

*Texture*.—Thick, leathery.

*Shape*.—Round.

*Form*.—Tips slightly recurved; edges are slightly quilled to moderately quilled.

*Arrangement*.—Imbricated. Petaloids in the center are few, averaging 1.3 per flower, and averaging 13 mm in length and 4 mm in width.

*Persistence*.—Drop off cleanly.

*Lastingness*.—On the plant: Long (nine to ten days). As a cut flower: Very long sixteen to nineteen days).

Reproductive parts:

*Anthers*.—Size: Medium. Quantity: Many. Color: Yellow. Arrangement: Regular around styles.

*Filaments*.—Color: Yellow.

*Pollen*.—Color: Gold Yellow.

*Styles*.—Color: Reddish.

*Stigmas*.—Color: Greenish-white.

Plant:

*Form*.—Bush.

*Growth*.—Very vigorous; upright; branching; KORmiller is a very vigorous, upright, and free-branching plant reaching 5½ feet in height and 3½ feet in width in six months of growing in a greenhouse. Height is controlled at six feet by regular harvest of flowers.

Foliage:

*Number of leaflets on normal mid-stem leaves*.—Five.

*Size*.—Large. (6½"×4¾").

*Quantity*.—Abundant.

*Color*.—New foliage: Upper and lower surfaces: Greyed-Purple Group 184B. Upper surface rapidly becomes green. On lower surface the Greyed-Purple Group 184B is quite persistent taking several more days to turn green. Old foliage: Upper surface: Green Group 139A. Lower surface: Green Group 137C.

*Shape*.—Pointed oval.

*Texture*.—Upper side: Leathery.

*Edge*.—Serrated.

*Serration*.—Single, small.

*Petiole Rachis*.—Color: Reddish.

*Petiole Underside*.—Smooth.

*Stipules*.—Medium (⅝"); serrated, bearded. Disease Resistance: Resistant to mildew under normal growing conditions at Sparrieshoop, Germany and Somis, Calif.

Wood:

*New wood*.—Color: Reddish (Greyed Orange 176A), quickly turning green. Bark: Smooth.

*Old wood*.—Color: Green (Green Group 137A). Bark: Smooth.

Prickles:

*Quantity*.—On main canes from base: Few (averages less than 1 per 12 inches of stem; lower part of canes may have more thorns). On laterals from main canes: Few.

*Form*.—Short (¼"); hooked slightly downward.

*Color when young*.—(Greyed Orange 176B; Old prickles: Greyed Orange 173D).

Small prickles:

*Quantity*.—On main stalks: None. On laterals: None.

I claim:

1. A new and distinct variety of rose plant of the floribunda class, substantially as herein shown and described, characterized particularly as to novelty by very attractive, pastel pink flower color, few thorns, long vase life, and high production of cut roses, on strong, straight stems.

* * * * *

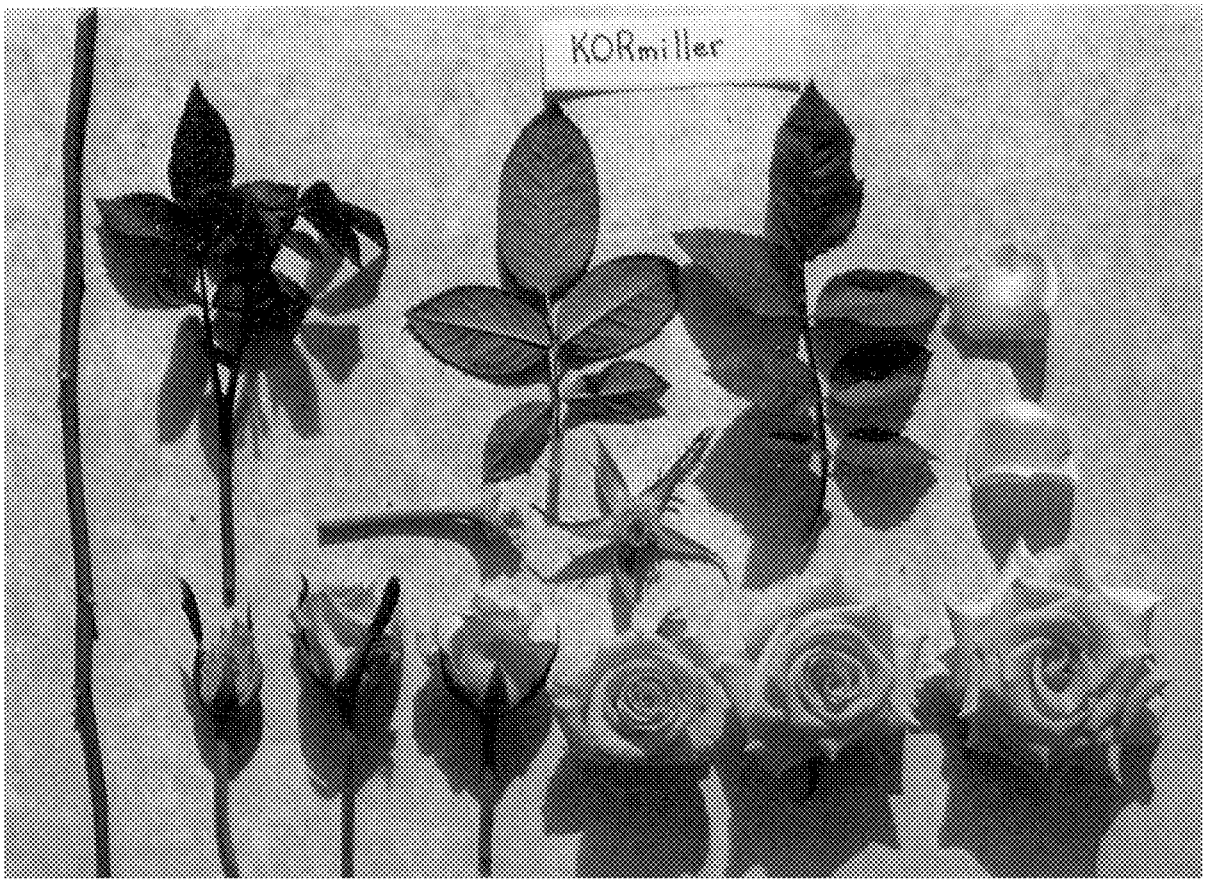
KORmiller